(12) United States Patent
Onishi et al.

(10) Patent No.: US 7,666,174 B2
(45) Date of Patent: Feb. 23, 2010

(54) DISPOSABLE DIAPER

(75) Inventors: Kazuaki Onishi, Kagawa (JP); Yusuke Kawakami, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 343 days.

(21) Appl. No.: 10/830,426

(22) Filed: Apr. 23, 2004

(65) Prior Publication Data

US 2006/0184151 A1    Aug. 17, 2006

(30) Foreign Application Priority Data

Apr. 24, 2003   (JP)   ............................ 2003-119964

(51) Int. Cl.
 *A61F 13/15*   (2006.01)
 *A61F 13/20*   (2006.01)
(52) U.S. Cl. ........................... 604/385.27; 604/385.01; 604/378
(58) Field of Classification Search ............ 604/385.01, 604/385.24–385.3
 See application file for complete search history.

(56) References Cited

U.S. PATENT DOCUMENTS

| | | | |
|---|---|---|---|
| 4,935,021 A * | 6/1990 | Huffman et al. | 604/385.26 |
| 2002/0151861 A1* | 10/2002 | Klemp et al. | 604/385.19 |

FOREIGN PATENT DOCUMENTS

| | | |
|---|---|---|
| JP | 8-196565 | 8/1996 |
| JP | 2000-296148 | 10/2000 |

* cited by examiner

*Primary Examiner*—Michele Kidwell
(74) *Attorney, Agent, or Firm*—Morrison & Foerster LLP

(57) ABSTRACT

Here is disclosed a disposable diaper, which includes a liquid-absorbent zone in a crotch region having first through fourth sections. A stiffness of the first and second sections formed from top- and backsheets is lower than a stiffness of the third and fourth sections formed from the top- and backsheets and an absorbent core. Stretchably elastic members extending in a longitudinal direction are contractibly attached to the fourth section. A liquid-absorbent zone in the crotch region is formed with a concavity (feces pocket) as the fourth section contract in the longitudinal direction under a contractile force of the elastic members.

13 Claims, 9 Drawing Sheets

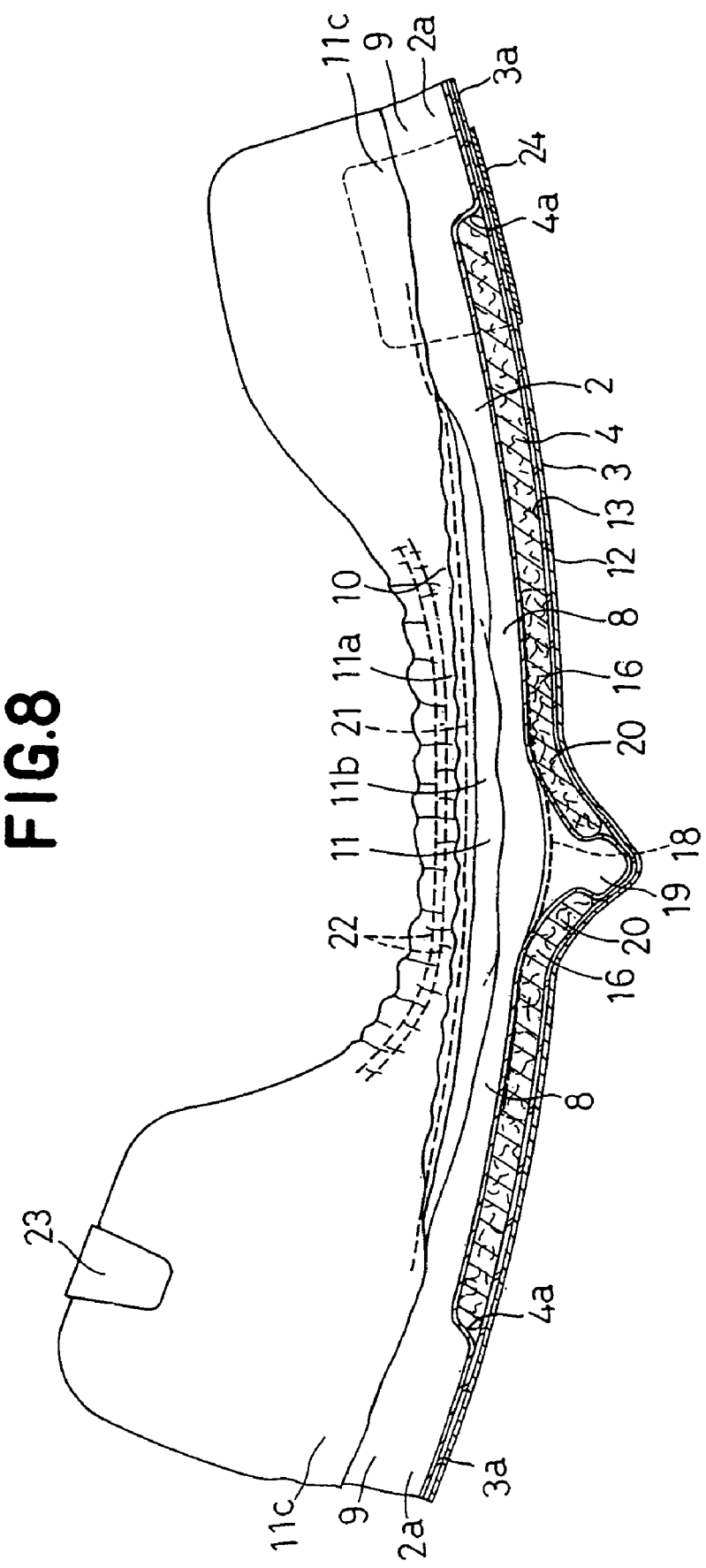

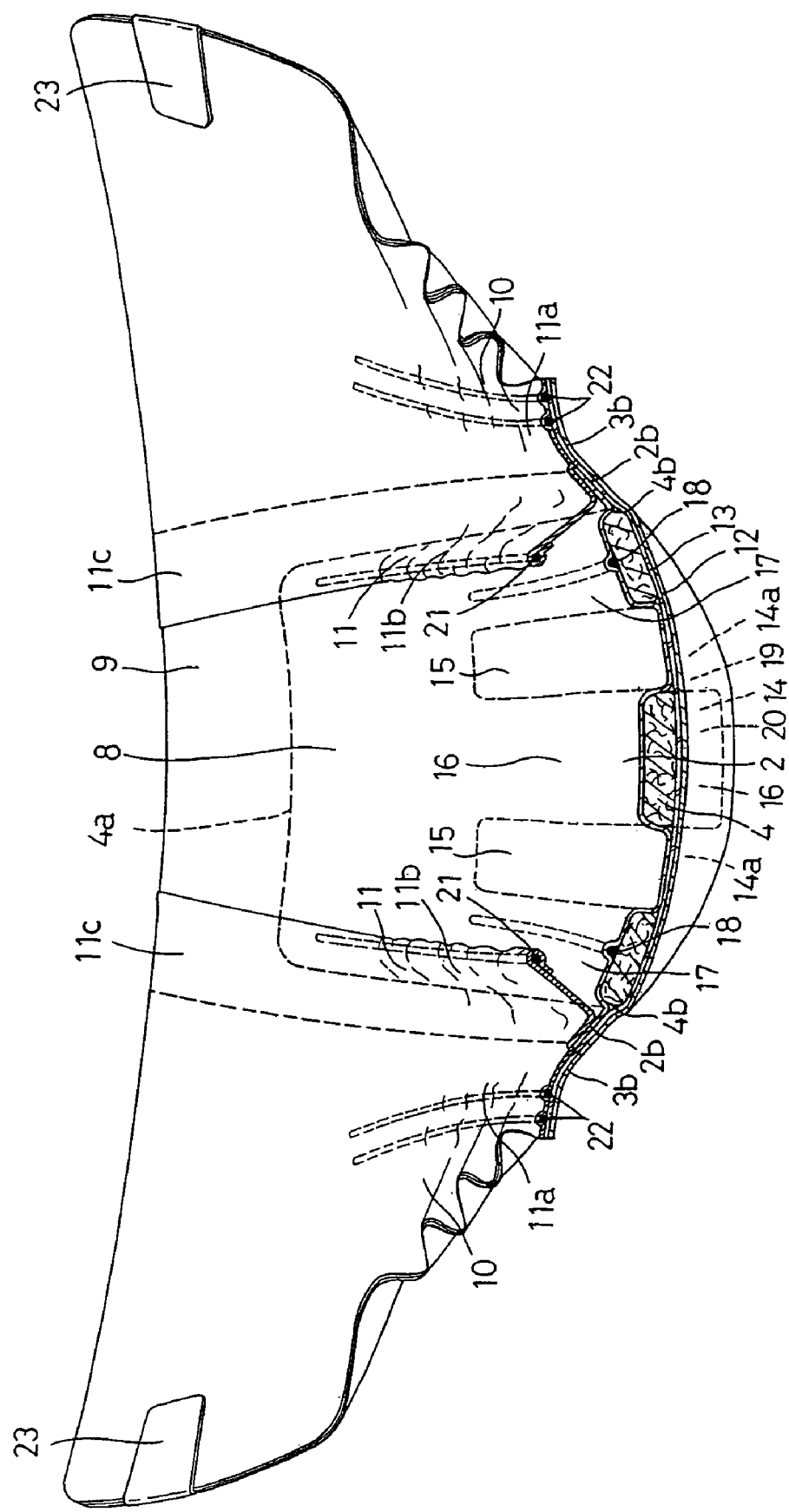

DISPOSABLE DIAPER

BACKGROUND OF THE INVENTION

The present invention relates to disposable diapers for absorbing and containing bodily discharges.

Conventional disposable diapers, for example, diapers disclosed in Japanese Patent Application Publication No. 1996-196565A (Citation 1) and in Japanese Patent Application Publication No. 2000-296148A (Citation 2) comprise a liquid-pervious topsheet facing a wearer's skin, a liquid-impervious backsheet facing away from the wearer's skin and a liquid-absorbent core interposed between these two sheets so as to configure, a front waist region, a rear waist region and a crotch region extending between these two waist regions. A liquid-absorbent zone is formed in the front and rear waist regions and the crotch region in which a liquid-absorbent function of the core is effective and a feces pocket is formed.

In the diaper disclosed in Citation 1, the absorbent core comprises an upper core and a lower core underlying the upper core. In a crotch region, the upper core comprises, in turn, front and rear cores spaced apart from and opposed to each other in a longitudinal direction. The topsheet covering an outer surface of the upper core is folded toward the lower core in the crotch region and tucked between the upper and lower cores so that a pocket for feces (feces pocket) discharged by a wearer may be formed between the upper and lower cores.

The diaper disclosed in Citation 2 has end flaps lying longitudinally outside the liquid-absorbent zone and extending in the transverse direction and a pair of side flaps lying transversely outside the liquid-absorbent zone and extending in the longitudinal direction. In the crotch region, the side flaps are formed with a pair of darts, respectively, extending in the transverse direction and defining therebetween a concave (feces pocket) which is concave downward in the thickness direction of the diaper.

In the diaper disclosed in Citation 1, the core comprises the upper core and the lower core placed on the upper core in a thickness direction of the diaper and inevitably a bulkiness of such double core gives a wearer a feeling of discomfort. In the diaper disclosed in Citation 2, the top- and backsheets are drawn inward in the longitudinal direction and bonded to each other to form the side flaps with darts and these darts function to close opening of a concavity formed therebetween. In this diaper, the opening of the concavity is apt to be closed. If the opening of the concavity is closed, the concavity will no more function to receive feces.

SUMMARY OF THE INVENTION

It is an object of the present invention to provide a disposable diaper improved so that no feeling of discomfort is experienced by the wearer and the liquid-absorbent zone in the crotch region can be formed with the feces pocket having no anxiety that the opening of this feces pocket might be unintentionally closed.

According to the present invention, there is provided a disposable diaper comprising: a liquid-pervious topsheet facing a wearer's skin, a liquid-impervious backsheet facing away from the wearer's skin and a liquid-absorbent core interposed between these two sheets so as to configure, a front waist region, a rear waist region and a crotch region extending between these two waist regions wherein a liquid-absorbent zone is formed in the front and rear waist regions and the crotch region in which a liquid-absorbent function of the absorbent core is effective.

The liquid-absorbent zone in the crotch region has a relatively flexible first section which extends across the crotch region at a longitudinal middle thereof, a pair of relatively flexible second sections lying transversely outside transversely opposite sides of the first section and longitudinally extending toward at least one of the front and rear waist regions, a pair of third section lying between the second sections and extending in the longitudinal direction and a pair of fourth sections lying transversely outside respective the second sections and extending in the longitudinal direction. The first and second sections have a stiffness lower than that of the third and fourth sections and stretchably elastic members extending in the longitudinal direction are contractibly attached to at least the fourth sections of the first, second and fourth sections. A contractile force of the elastic members causes the fourth sections to contract in the longitudinal direction whereupon the liquid-absorbent zone in the crotch region is formed with a feces pocket which is concave downward in the thickness direction of the diaper.

The present invention includes the following preferred embodiments.

The first and second section are formed from the top- and backsheets except the core and the third and fourth sections are formed from the top- and backsheets and the core.

The first through fourth sections are formed from the top- and backsheets and the core and a stiffness of the core is lower in the first and second sections than in the third and fourth sections.

A liquid-absorbent function of the core is higher in the third section than in the fourth section.

A Gurley stiffness of the first and second sections is in a range of $0.98 \times 10^{-7}$ to $19.6 \times 10^{-7}$ N and a Gurley stiffness of the third and fourth sections is in a range of $9.8 \times 10^{-7}$ to $196 \times 10^{-7}$ N.

BRIEF DESCRIPTION OF THE DRAWINGS

FIG. 8 is a sectional view taken along the line VIII-VIII in FIG. 7; and

FIG. 9 is a sectional view taken along the line IX-IX in FIG. 7.

DETAILED DESCRIPTION OF THE PREFERRED EMBODIMENTS

Details of a disposable diaper according to the present invention will be more fully understood from the description given hereunder with reference to the accompanying drawings.

Figure 1:
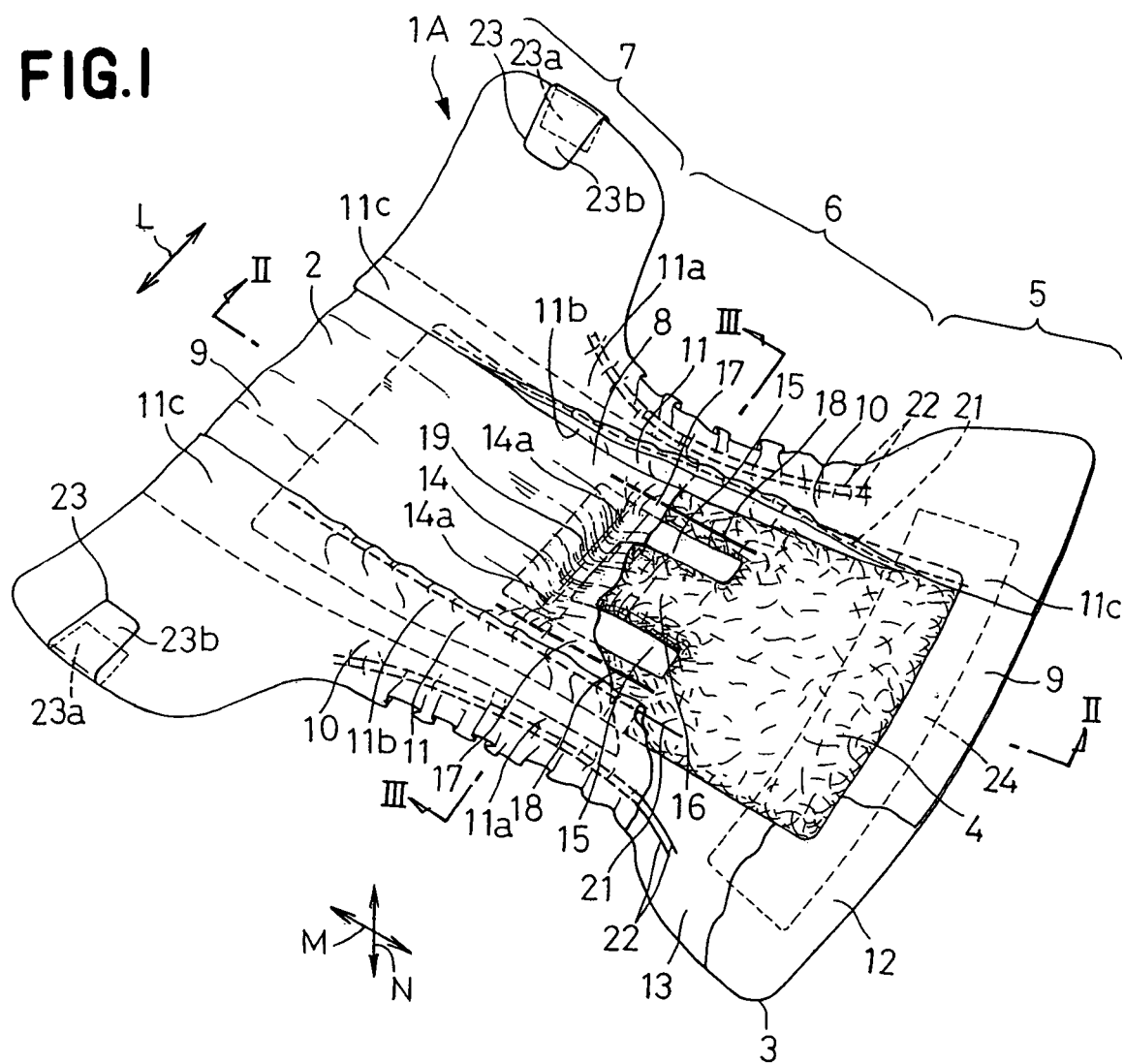
FIG. 1 is a partially cutaway perspective view showing one embodiment of a diaper according to the invention.
Figure 2:
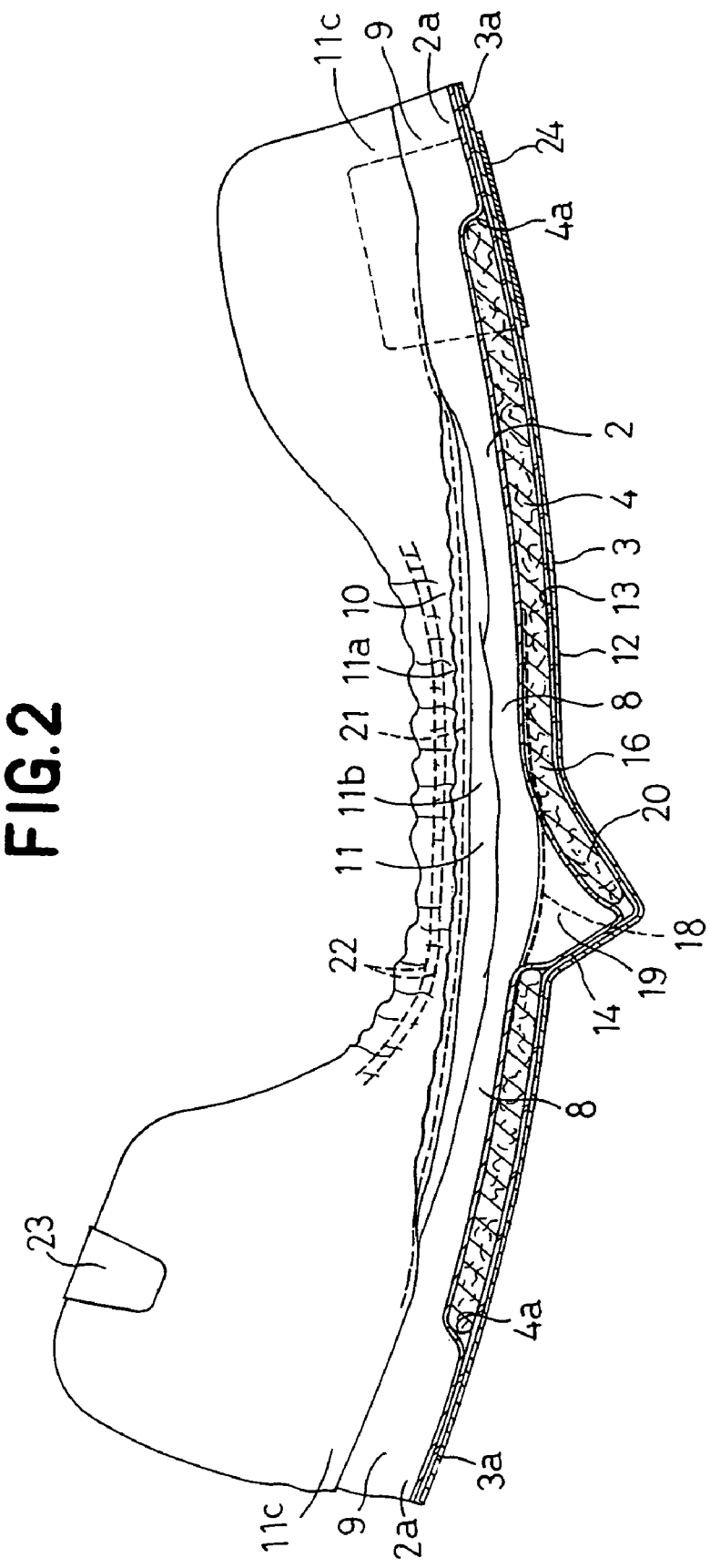
FIG. 2 is a sectional view taken along the line II-II in FIG. 1.
Figure 3:
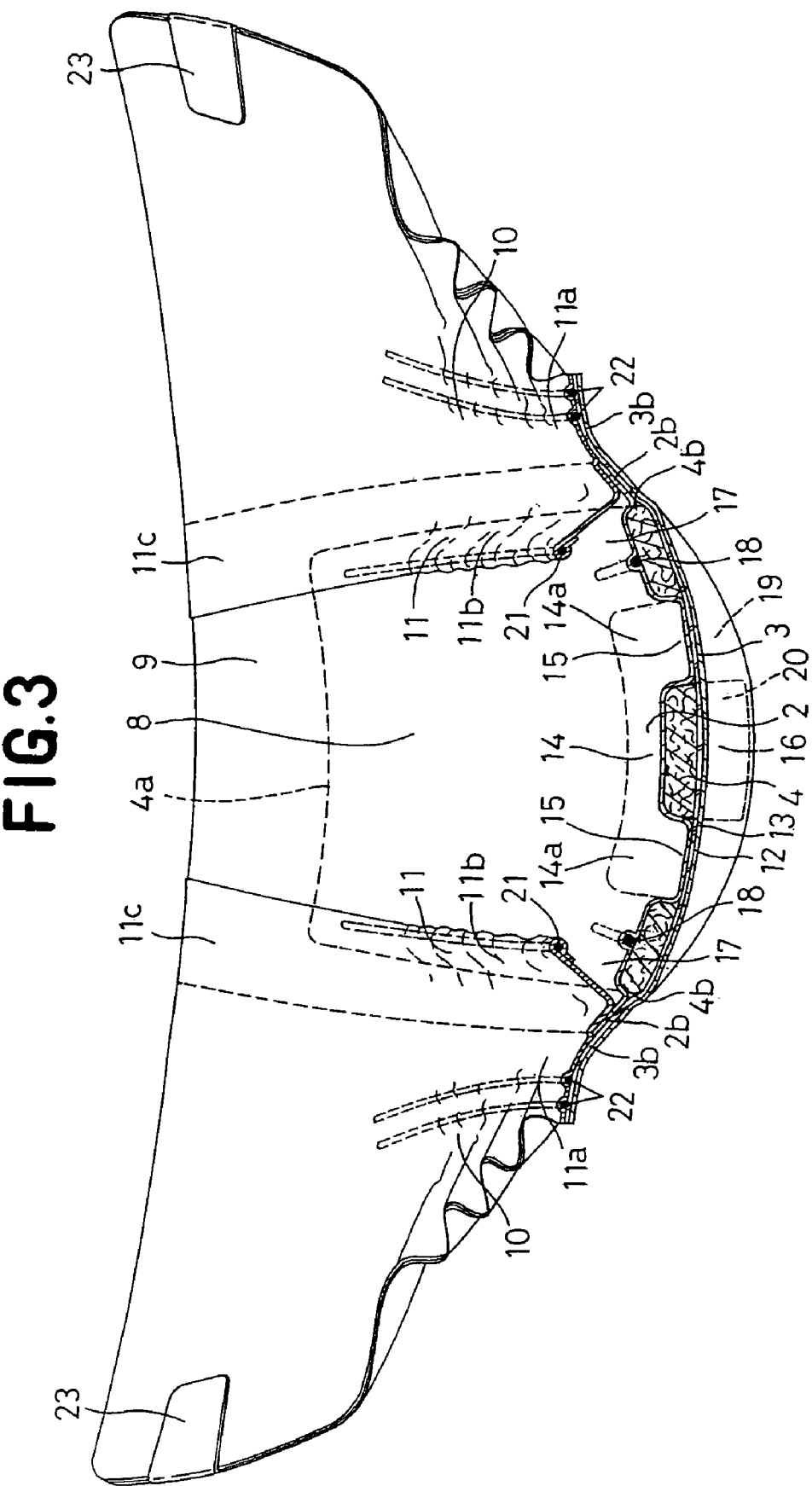
FIG. 3 is a sectional view taken along the line III-III in FIG. 1.

FIG. 1 is a partially cutaway perspective view of a diaper 1A according to one embodiment of the invention, FIG. 2 is a sectional view taken along the line II-II in FIG. 1 and FIG. 3 is a sectional view taken along the line III-III in FIG. 1. In FIG. 1, a transverse direction is indicated by an arrow L, a longitudinal direction is indicated by an arrow M and a thickness direction is indicated by an arrow N.

A diaper 1A comprises a liquid-pervious topsheet 2 facing a wearer's skin, a liquid-impervious backsheet 3 facing away from the wearer's skin and a liquid-absorbent core 4 interposed between these two sheets 2, 3. From a viewpoint of its configuration, the diaper 1A is composed, as viewed in the longitudinal direction, of a front waist region 5, a rear waist region 7 and a crotch region 6 extending between these two waist regions 5, 7. The illustrated diaper 1A is of the so-called open-type characterized in that the front and rear waist regions 5, 7 are connected to each other immediately before or after the diaper 1A is put on the wearer's body. The diaper 1A has a liquid-absorbent zone 8 in which the core 4 functions to absorb body fluids discharged from the wearer, a pair of end flaps 9 lying outside longitudinally opposite ends of the liquid-absorbent zone 8 and extending in the transverse direction and a pair of side flaps 10 lying outside transversely opposite side edges of the liquid-absorbent zone 8 and extending in the longitudinal direction. The liquid-absorbent zone 8 is formed in the front and rear waist regions 5, 7 and the crotch region 6.

In the crotch region 6, the side flaps 10 describe circular arcs which are convex inwardly as viewed in the transverse direction of the diaper 1A, so the diaper 1A has a generally hourglass-like planar shape. A pair of liquid-impervious leak-barrier sheets 11 extending in the longitudinal direction are attached to the respective side flaps 10. The backsheet 3 is formed from a composite sheet composed of a hydrophobic fibrous nonwoven fabric 12 and a breathable liquid-impervious plastic film 13 laminated on each other.

The liquid-absorbent core 4 comprises a mixture of fluff pulp and super-absorbent polymers or a mixture of fluff pulp fibers, super-absorbent polymers and thermoplastic synthetic resin fibers, in any case, compressed to a desired thickness. With a consequence, the core 4 has a certain degree of flexibility but its stiffness is higher than those of the top- and backsheets 2, 3, that is, a semi-rigidity. In other words, the liquid-absorbent zone 8 in which the core 4 is present has a stiffness higher than those of the end flaps 9 and the side flaps 10 in which the core 4 is absent.

Sections of the liquid-absorbent zone 8 lying in the front and rear waist regions 5, 7 are formed from the top- and backsheets 2, 3 and the liquid-absorbent core 4. In the front and rear waist regions 5, 7, the core 4 is permanently bonded between the top- and backsheets 2, 3. A section of the liquid-absorbent zone 8 has first through fourth sections 14, 15, 16, 17.

The first section 14 lies at a longitudinal middle of the crotch region 6 and extends in the transverse direction. The second sections 15 are transversely spaced apart from each other by a given dimension and longitudinally extending from transversely opposite side edges 14a toward the front waist region 5. The first section 14 and the pair of second sections 15 are formed from the top- and backsheets 2, 3, i.e., the core 4 is absent therein. In these first and second sections 14, 15, the top- and backsheets 2, 3 have their inner surfaces permanently bonded to each other.

The third section 16 is interposed between the pair of second sections 15 and extends from the first zone 14 toward the front waist region 5. The third section 16 lies in a generally front half of the crotch region 6. The pair of fourth sections 17 respectively lie laterally outside the respective second sections 15 and extend between the side flaps 10 and the second sections 15, respectively, in the longitudinal direction. The third section 16 and the pair of fourth sections 17 are formed from the top- and backsheets 2, 3 and the core 4. Stretchably elastic members 18 extending in the longitudinal direction are contractibly attached to the respective fourth sections 17. These elastic members 18 are interposed between the topsheet 2 and the core 4 and permanently bonded to the inner surface of the topsheet 2 and to the core 4.

The core 4 in the third section 16 is contiguous to the core 4 in the front waist region 5. In the third section 16, the core 4 is bonded neither to the topsheet 2 nor to the backsheet 3 and left free from these sheets 2, 3. It should be noted here that the core 4 in the third section 16 may be permanently bonded to the inner surfaces of the top- and backsheets 2, 3 or to the inner surface of the top- or backsheet 2, 3. The core 4 in the fourth sections 17 is contiguous to the core 4 in the front and rear waist regions 5, 7. The core 4 in the fourth sections 17 is permanently bonded to the inner surfaces of the top- and backsheets 2, 3.

The core 4 in the third section 16 has a liquid-absorbing function higher than a liquid-absorbing function of the core 4 in the fourth sections 17. To ensure that the core 4 in the third section 16 has the liquid-absorbing function higher than the liquid-absorbing function achieved by the core 4 in the fourth sections 17, the core 4 in the third section 16 may be formed to have a thickness larger than the thickness of the core 4 in the fourth sections 17 so far as the core 4 in the these sections 16, 17 has a uniform density and the core 4 in the third section 16 may be formed to have a density higher than a density of the core 4 in the fourth sections 17 so far as these sections 16, 17 have a uniform thickness. To increase a density of the core 4, a basis weight of fluff pulp fibers and/or thermoplastic synthetic resin fibers may be increased or a content of super-absorbent polymers may be increased. Alternatively, the core 4 in the third section 16 may be dimensioned to have a thickness larger than a thickness of the core 4 in the fourth sections 17 and the core 4 in the third section 16 may be formed to have a density higher than a density of the core 4 in the fourth sections 17. Further an alternative embodiment is also possible according to which the core 4 in the third and fourth sections 16, 17 achieve perfectly matched liquid-absorbing functions.

The core 4 is absent in the first and second sections 14, 15, so a stiffness of these sections 14, 15 is sufficiently lower than those of the third and fourth sections 16, 17 to facilitate these sections 16, 17 to be flexed in comparison to the third and fourth sections 16, 17, i.e., high flexibility. In the liquid-absorbent zone 8 lying in the crotch region 6, a contractile force of the elastic members 18 in the longitudinal direction causes the fourth sections 17 to contract in the longitudinal direction and causes the third section 16 to get near to the first section 14. In the liquid-absorbent zone 8 lying in the crotch region 6, the first and second sections 14, 15 are longitudinally flexed downward in the thickness direction to form a concavity 19, i.e., feces pocket. This concavity 19 is defined by the first section 14 and a part of the second sections 15 between the pair of fourth sections 17. As will be apparent from FIG. 2, a portion 20 of the third section 16 lying adjacent the first section 14 slopes downward as viewed in the thickness direction of the diaper 1 and constitute a part of the concavity 19.

Each of the leak-barrier cuffs 11 has a proximal portion 11a attached to the associated one of the flaps 10 and extending in the longitudinal direction, a distal portion 11b normally biased to rise up above the topsheet 2 and extending in the longitudinal direction and longitudinally opposite ends 11c lying on the end flaps 9, respectively, and collapsed inward as viewed in the transverse direction of the diaper 1A. A stretchably elastic member 21 extending in the longitudinal direction is permanently attached to the leak-barrier sheet 11 along an upper edge of the distal portion 11b so that the elastic member 21 can contract in the longitudinal direction. In the leak-barrier sheet 11, the elastic member 21 contracts as the diaper 1A is bowed in the longitudinal direction with the topsheet 2 inside, and a contractile force of the elastic member 21, in turn, biases the distal portion 11b to rise up above the topsheet 2 so that the distal portion 11b may form a barrier against urine and/or feces.

As illustrated by FIG. 2, the end flaps 9 are formed from longitudinally opposite end portions 2a of the topsheet 2 and longitudinally opposite end portions 3a of the backsheets 3 extending outward beyond the longitudinally opposite ends 4a of the core 4, respectively, in the longitudinal direction. In the end flaps 9, these end portions 2a, 3a of the top- and backsheets 2, 3 are put flat and permanently bonded together. The longitudinally opposite ends 11c of the respective leak-barrier sheets 11 are permanently bonded to the outer surface of the topsheet 2.

As illustrated by FIG. 3, the side flaps 10 are formed from transversely opposite lateral portions 2b of the topsheet 2 and the transversely opposite lateral portions 3b of the backsheet 3 extending outward in the transverse direction beyond the opposite side edges 4b of the core 4 and the proximal portions 11a of the respective leak-barrier sheets 11. In each of the side flaps 10, the lateral portion 2b of the topsheet 2 extends outward in the transverse direction slightly beyond the associated side edge 4b of the core 4 and, beyond the lateral portion 2b of the topsheet 2, the lateral portion 3b of the backsheet 3 as well as the proximal portion 11a of the leak-barrier sheet 11 extend further outward in the transverse direction. In each of the side flaps 10, the respective lateral portions 2b, 3b, 11a of these sheets 2, 3, 11 are put flat and permanently bonded one to another. A plurality of leg elastic members 22 extending in the longitudinal direction are contractibly attached to each of the side flaps 10. These leg elastic members 22 are interposed between the lateral portion 3b of the backsheet 3 and the proximal portion 11a of the leak-barrier sheet 11 and permanently bonded to the respective inner surfaces of the portions 3b, 11a of these sheets 3, 11.

In the rear waist region 7, the side flaps 10 are provided with flexible tape fasteners 23 made of a plastic film attached thereto, respectively. Each of this tape fasteners 23 has a proximal portion 23a and a distal portion 23b both extending in the transverse direction. The proximal portion 23a is interposed between the lateral portion 3b of the backsheet 3 and the proximal portion 11a of the leak-barrier sheet 11 and permanently bonded to the inner surface of these portions 3b, 11a. The distal portion 23b is coated on its inner surface with adhesives (not shown). The distal portion 23b is folded inward as viewed in the transverse direction of the diaper 1A and temporarily bonded to a release sheet (not shown) permanently bonded to the proximal portion 11a of the leak-barrier sheet 11 by means of adhesives. The front waist region 5 is provided with a flexible target tape strip 24 attached thereto so that the distal portions 23b of the respective tape fasteners 23 may be detachably anchored thereon. The target tape strip 24 is made of a plastic film and has a rectangular shape which is relatively long in the transverse direction. The target tape strip 24 is permanently bonded to the outer surface of the backsheet 3.

Immediately before or after the diaper 1A is put on a wearer's body, the side flaps 10 in the rear waist region 7 may be placed on the outer surfaces of the side flaps 10 in the front waist region 5 and the distal portions 23b of the respective tape fasteners 23 may be anchored on the target tape strip 24 to connect the front and rear waist regions 5, 7 to each other. The diaper 1A having the front and rear waist regions 5, 7 connected in this manner is formed with a waist-hole and a pair of leg-holes (not shown).

In the crotch region 5 of this diaper 1A, the liquid-absorbent zone 8 is formed with the concavity 19 directed downward in the thickness direction so that feces discharged by the wearer may be contained in this concavity 19. In the diaper 1A, the core 4 which is present in the rear waist region 7, and the third and fourth sections 16, 17 defines a peripheral wall surrounding the concavity 19 and thereby prevents loose passage contained in the concavity 19 from flowing to the front and rear waist regions 5, 7 as well as to the side flaps 10. Moisture contained in feces discharged by the wearer is absorbed by the core 4 which is present in the third and fourth sections 16, 17 after has permeated the topsheet 2. Urine is absorbed by the core 4 which is present in the front waist region 5.

The core 4 has a liquid-absorbing function higher in the third section 16 than in the fourth sections 17. This means that a large moisture content in loose passage can be rapidly absorbed by the third section 16 of the core 4 before loose passage flows to the front and rear waist regions 5, 7 as well as to the side flaps 10 and consequently it is possible to reliably prevent loose passage from flowing to the front and rear waist regions 5, 7 as well as to the side flaps 10.

The third section 16 of the core 4 is bonded neither to the topsheet 2 neither to the backsheet 3, so the contractile force of the elastic members 18 is not significantly restrained by the stiffness of the core 4 in the third section 16 as it is the case in which the core 4 in the third section 16 is permanently bonded to both the topsheet 2 and the backsheet 3. Consequently, the core 4 in the fourth section 17 smoothly contracts in the longitudinal direction and the liquid-absorbent zone 8 in the crotch region 6 reliably forms the concavity 19.

The first and second sections 14, 15 have a Gurley stiffness in a range of $0.98 \times 10^{-7}$ to $19.6 \times 10^{-7}$ N and the third and fourth sections 16, 17 have a Gurley stiffness in a range of $9.8 \times 10^{-7}$ to $196 \times 10^{-7}$ N. If the Gurley stiffness of the first and second sections 14, 15 exceeds $19.6 \times 10^{-7}$, flexibility of these sections 14, 15 will be deteriorated and it may be sometimes impossible to form the liquid-absorbent zone 8 in the crotch region 6. If the Gurley stiffness of the third and fourth sections 16, 17 is less than $9.8 \times 10^{-7}$, on the other hand, the fourth section will excessively contract to close an opening of the concavity 19, depending on a stretch or tensile stress and a contraction percentage of the elastic members 18. If the Gurley stiffness of the third and fourth sections 16, 17 exceeds $196 \times 10^{-7}$, the contractile force of the elastic members 18 will be restrained by the stiffness of these sections 16, 17, not only making it difficult to form the liquid-absorbent zone 8 in the crotch region 6 with the concavity 19 but also hardening the third and fourth sections 16, 17. In consequence, these sections 16, 17 will create a feeling of discomfort against a wearer's skin. The Gurley stiffness of these sections 14, 15, 16, 17 was measured by a method as follows:

(1) The first through fourth sections 14, 15, 16, 17 were cut away from the diaper 1A to prepare rectangular samples for measurement of Gurley stiffness each dimensioned of 38 mm×25 mm.

(2) Measurement of Gurley stiffness was carried out using the Gurley stiffness tester according to the procedures as follows: (a) one end of the sample was held by chuck of the tester in such a manner that the other end was maintained in engagement with a pivot rod of a pendulum; (b) the tester was initialized by loading an auxiliary weight so that the tester scale pointed a reading in a range of 3 to 6; and (c) the tester was turned on and a scale reading of the moment at which the pivot rod of the pendulum was separated from the sample was recorded. Scale reading was recorded both for rightward test and leftward test.

(3) The Gurley stiffness was calculated by an equation of (a scale reading for rightward stiffness+a scale reading for leftward stiffness/2)×{((①)×1+(②)×2+(③)×3)/5}× (longitudinal dimension (inch) of the sample/transverse dimension (inch)×9.88, where ①, ② and ③ respective represent positions of openings in which the respective weights were loaded, specifically ① represents g at a reading of 1 inch, ② represents g at a reading of 2 inches and ③ represents g at a reading of 2 inches. After calculation according to such equation, the Gurley stiffness was converted in N (Newton) unit.

Figure 4:
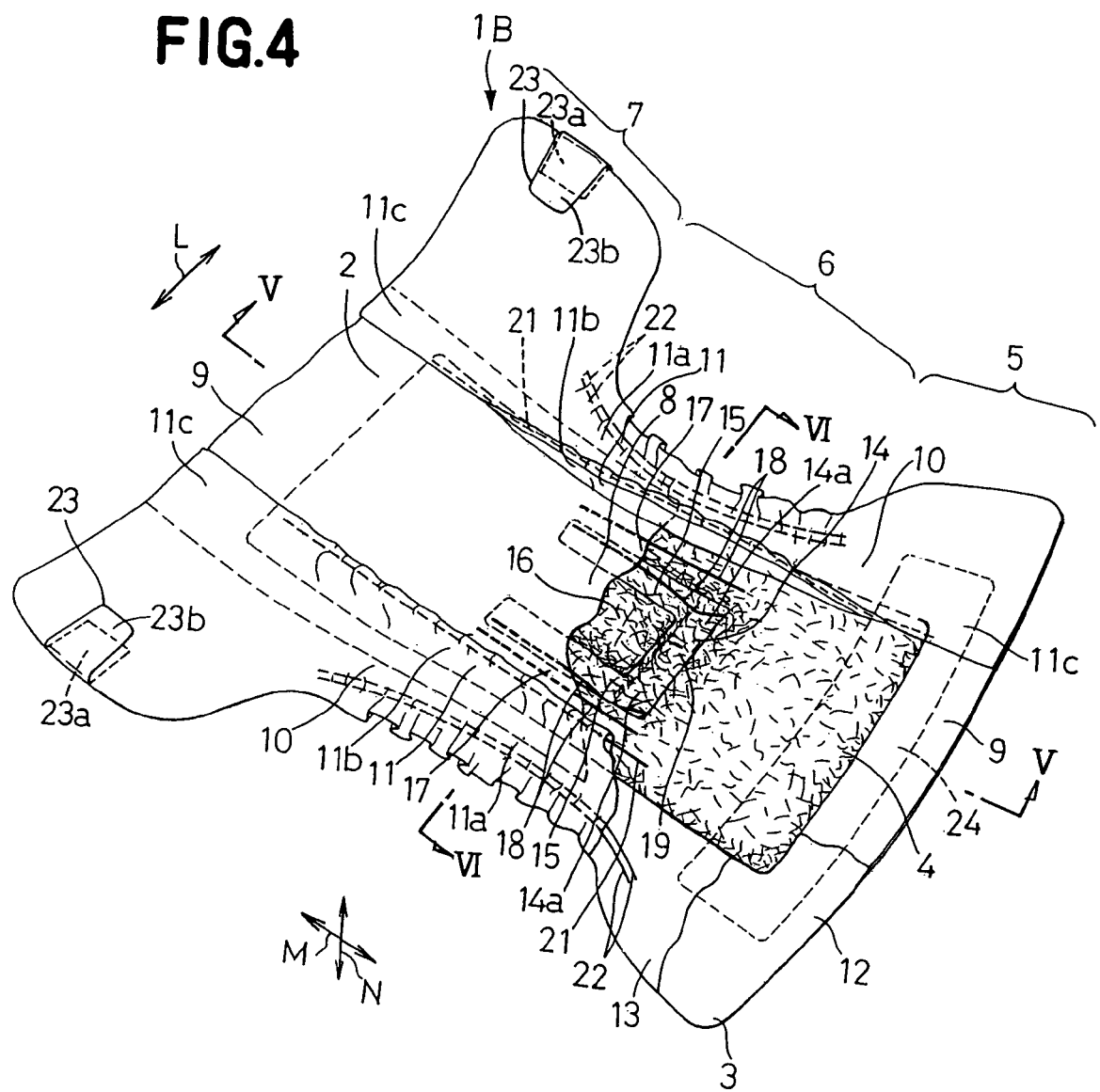
FIG. 4 is a partially cutaway perspective view showing another embodiment of the diaper according to the invention.
Figure 5:
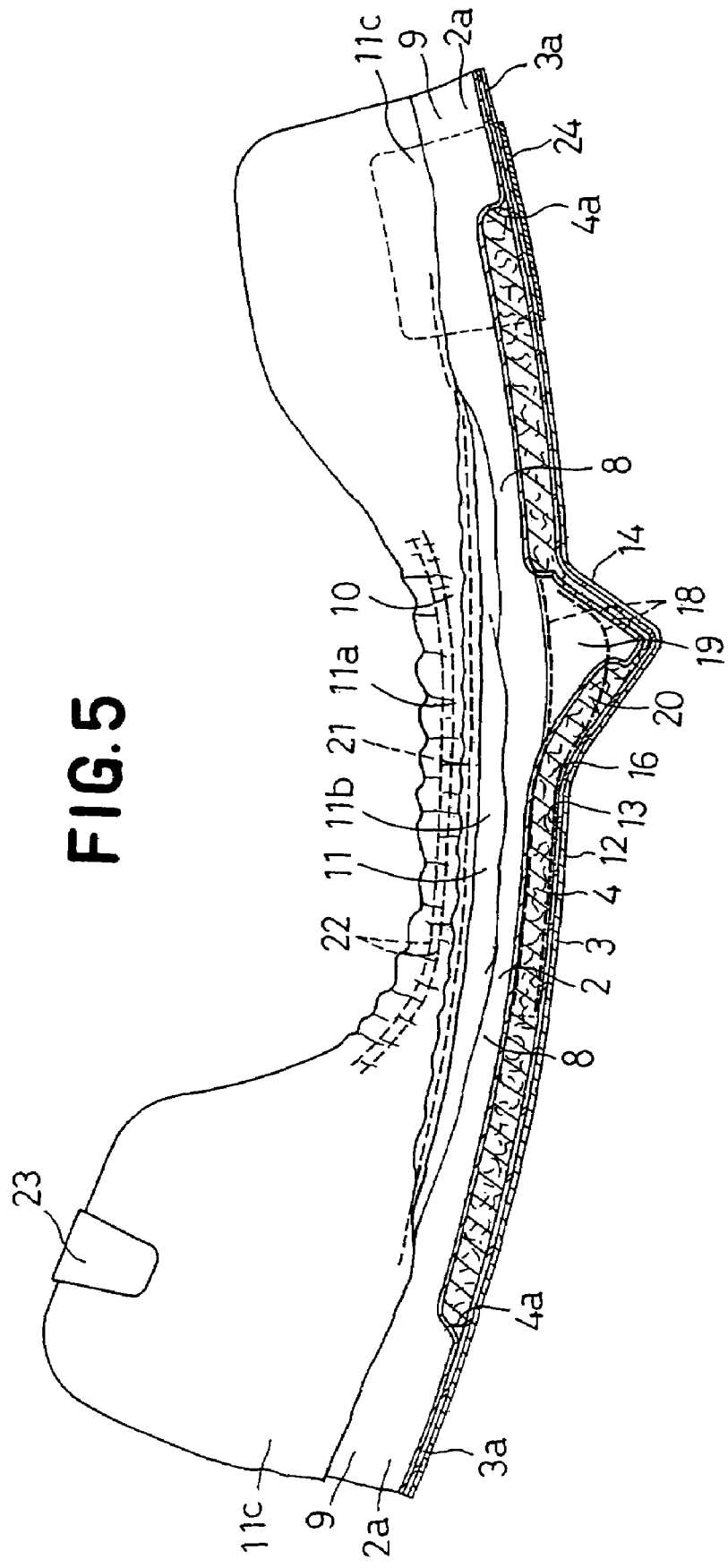
FIG. 5 is a sectional view taken along the line V-V in FIG. 4.
Figure 6:
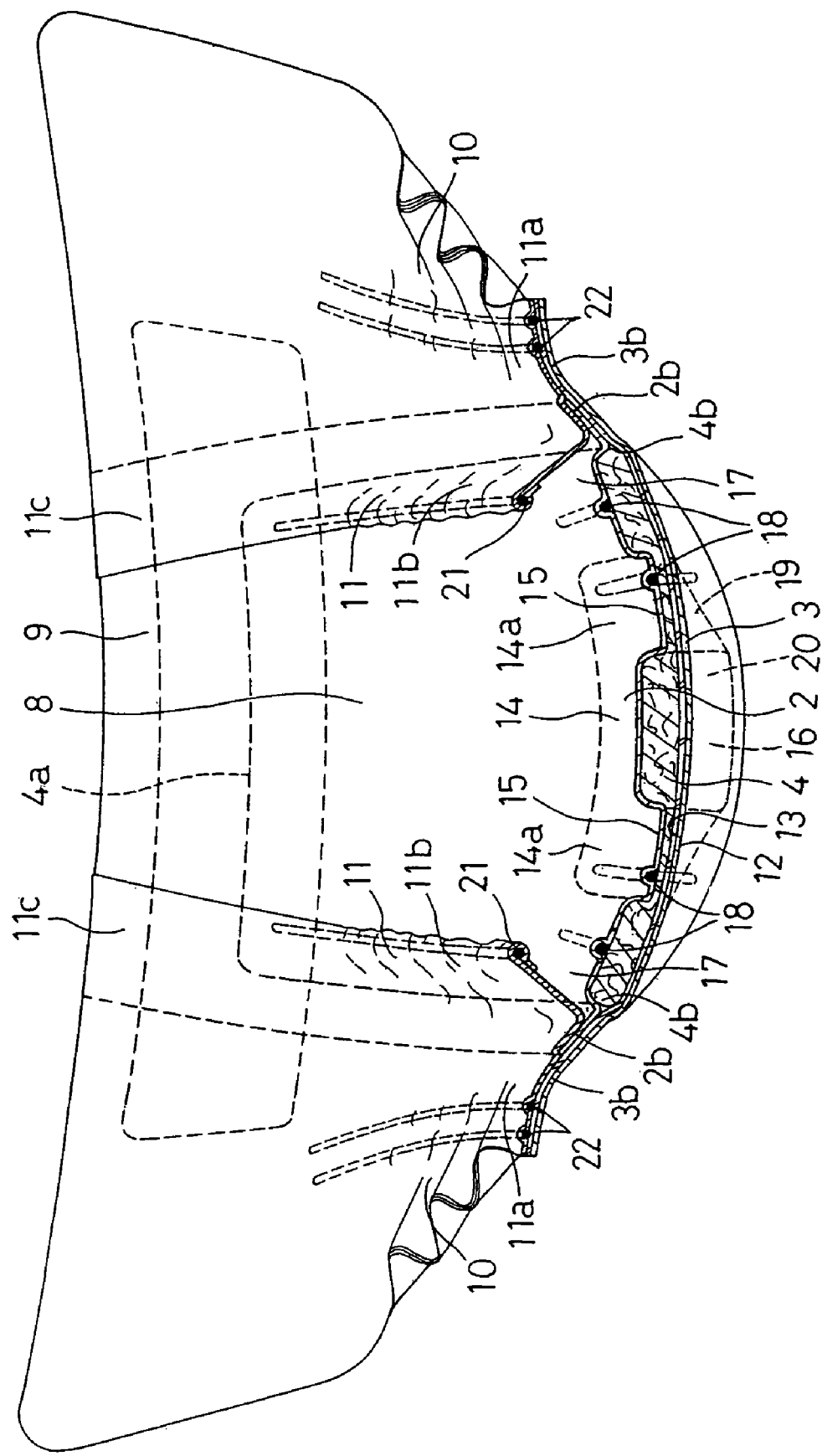
FIG. 6 is a sectional view taken along the line VI-VI in FIG. 4.

FIG. 4 is a partially cutaway perspective view of a diaper 1B according to another embodiment of the invention, FIG. 5 is a sectional view taken along the line V-V in FIG. 4 and FIG. 6 is a sectional view taken along the line VI-VI in FIG. 4. In FIG. 4, a transverse direction is indicated by an arrow L, a longitudinal direction is indicated by an arrow M and a thickness direction is indicated by an arrow N. FIGS. 5 and 6 correspond to the diaper 1B of FIG. 4 but not cutaway.

The diaper 1B comprises a liquid-pervious topsheet 2, a liquid-impervious backsheet 3 and the semi-rigid liquid-absorbent core 4 interposed between these two sheets 2, 3. The backsheet 3 as well as the core 4 are the same as those in FIG. 1. The diaper 1A is composed, as viewed in the longitudinal direction, of a front waist region 5, a rear waist region 7, a crotch region 6 extending between these two waist regions 5, 7. A liquid-absorbent zone 8 in which the core 4 functions to absorb body fluids discharged from the wearer, a pair of end flaps 9 extending in the transverse direction and a pair of side flaps 10 extending in the longitudinal direction. The liquid-absorbent zone 8 is formed in the front and rear waist regions 5, 7 and the crotch region 6 and has a stiffness higher than those of the end flaps 9 and the side flaps 10. The side flaps 10 are provided with a pair of liquid-impervious leak-barrier sheets 11.

Sections of the liquid-absorbent zone 8 lying in the front and rear waist regions 5, 7 are formed from the top- and backsheets 2, 3 and the core 4. In the front and rear waist regions 5, 7, the core 4 is permanently bonded to the inner surfaces of the top- and backsheets 2, 3. The liquid-absorbent zone 8 in the crotch region 6 has a first section 14 lies at a longitudinal middle of the crotch region 6 and extending in the transverse direction, a pair of second sections 15 longitudinally extending from transversely opposite side edges 14a of the first section 14a toward the rear waist region 7, a third section 16 lying between the second sections 15 and longitudinally extending from the first section 14 toward the rear waist region 7 and a pair of fourth sections 17 lying transversely outside the respective second sections 15 and extending in the longitudinal direction.

The first section 14 and the pair of second sections 15 are formed from the top- and backsheets 2, 3 and the core 4. In these first and second sections 14, 15, the top- and backsheets 2, 3 have their inner surfaces permanently bonded to each other. Stretchably elastic members 18 extending in the longitudinal direction are contractibly bonded to the first and second sections 14, 15. These elastic members 18 are interposed between the topsheet 2 and the core 4 and permanently bonded to the inner surface of the topsheet 2 and to the core 4.

The third section 16 lies in a generally front half of the crotch region 6. The pair of fourth sections 17 respectively lie between the respective side flaps 10 and the respective second sections 15. The third section 16 and the pair of fourth sections 17 are formed from the top- and backsheets 2, 3 and the core 4. In the third and fourth sections 16, 17, the core 4 is permanently bonded to the inner surfaces of the top- and backsheets 2, 3. The stretchably elastic members 18 extending in the longitudinal direction are contractibly attached to the respective fourth sections 17. These elastic members 18 are interposed between the topsheet 2 and the core 4 and permanently bonded to the inner surface of the topsheet 2 and to the core 4.

The third and fourth sections 16, 17 may be the same as each other in the liquid-absorbing function or, as in the diaper 1A of FIG. 1, the core 4 may have a liquid-absorbing function higher in the second section 16 than in the fourth sections 17.

The core 4 in the first and second sections 14, 15 have a thickness smaller than those of the core 4 lying in the front and rear waist regions 5, 7 as well as the core 4 in the third and fourth sections 16, 17. The core 4 in the first and second sections 14, 15 has a stiffness lower than that of the core 4 in the third and fourth sections 16, 17. The core 4 in the first and second sections 14, 15 may have a density lower than or same as that of the core 4 in the third and fourth sections 16, 17. The core 4 in the third and fourth sections 16, 17 may have a liquid-absorbing function higher than that of the core 4 in the first and second sections 14, 15.

Alternatively, the core 4 in the first and second sections 14, 15 may have the same thickness as the thickness of the core 4 in the third and fourth sections 16, 17. In this alternative case, a density of the core 4 in the first and second sections 14, 15 is adjusted to be lower than that of the core 4 in the third and fourth sections. Adjustment of a density of the core 4 may be achieved either by appropriately reducing a basis weight of fluff pulp fibers and/or thermoplastic synthetic resin fibers constituting the core 4 or appropriately decreasing a content of the super-absorbent polymers. Gurley stiffness values of the first through fourth sections 14, 15, 16, 17 as well as the method of measuring Gurley stiffness values of these sections 14, 15, 16, 17 are similar to those as have been described with reference to FIG. 1.

The core 4 in the first and second sections 14, 15 has a stiffness lower than the core 4 in the third and fourth sections 16, 17 and exhibits a Gurley stiffness in a range of 0.01 to 0.2 mg, so the core 4 is more flexible in the first and second sections 14, 15 than in the third and fourth sections 16, 17, i.e., high flexibility. In the liquid-absorbent zone 8 in the crotch region 6, a contractile force of the elastic members 18 in the longitudinal direction causes the fourth sections 17 to contract in the longitudinal direction and causes the third section 16 to get near to the first section 14. In the liquid-absorbent zone 8 in the crotch region 6, the first and second sections 14, 15 are longitudinally flexed downward in the thickness direction of the diaper 1B to form a concavity 19, i.e., feces pocket. This concavity 19 is defined by the first section 14 and a part of the second sections 15 between the pair of fourth sections 17. As will be apparent from FIG. 5, a portion 20 of the third section 16 lying adjacent the first section 14 slopes downward as viewed in the thickness direction of the diaper 1B and constitute a part of the concavity 19.

Each of the leak-barrier sheets 11 has a proximal portion 11a attached to the associated one of the side flaps 10 and extending in the longitudinal direction, a distal portion 11b normally biased to rise on the topsheet 2 and extending in the longitudinal direction and longitudinally opposite ends 11c lying on the end flaps 9, respectively, and collapsed inward as viewed in the transverse direction of the diaper 1A. A stretchably elastic member 21 extending in the longitudinal direction is permanently attached to the leak-barrier sheet 11 along an upper edge of the distal portion 11b so that the elastic member 21 can contract in the longitudinal direction.

The end flaps 9 are formed from longitudinally opposite end portions 2a of the topsheet 2 and longitudinally opposite end portions 3a of the backsheets 3. In the end flaps 9, these end portions 2a, 3a of the top- and backsheets 2, 3 are put flat and permanently bonded together. The longitudinally opposite fixed ends 11c of the respective leak-barrier sheets 11 are permanently bonded to the outer surface of the topsheet 2. The side flaps 10 are formed by transversely opposite lateral portions 2b of the topsheet 2 and the transversely opposite lateral portions 3b of the backsheet 3, and the fixed lateral portions 11a of the respective leak-barrier sheets 11. In each of the side flaps 10, the respective lateral portions 2b, 3b, 11a of these sheets 2, 3, 11 are put flat and permanently bonded one to another. A plurality of leg elastic members 22 extending in the longitudinal direction are contractibly attached to each of the side flaps 10.

In the rear waist region 7, the side flaps 10 are provided with flexible tape fasteners 23 each having a free end portion 23b coated with adhesives (not shown). The front waist region 5 is provided with a flexible target tape strip 24 which is relatively long in the transverse direction and attached thereto so that the free end portions 23b of the respective tape fasteners 23 may be detachably anchored thereon. The tape fasteners 23 and the target tape strip 24 are made of plastic film. The procedure for putting this diaper 1B on a wearer's body is the same as for the diaper 1A of FIG. 1.

In the crotch region 5 of this diaper 1B, the liquid-absorbent zone 8 is formed with the concavity 19 directed downward in the thickness direction so that feces discharged by the wearer of this diaper 1B maybe contained in this concavity 19. A difference of level as viewed in the thickness direction is defined between the core 4 lying in the first and second sections 14, 15, on one hand, and the core 4 lying in the front and rear waist regions 5, 7 as well as in the third and fourth sections 16, 17, on the other hand. The core 4 lying in the front waist region 5 and the third and fourth sections 16, 17 forms a peripheral wall surrounding the concavity 19 and such peripheral wall is effective to prevent loose passage contained in the concavity 19 from flowing to the front and rear waist regions 5, 7 and to the side flaps 10. Moisture contained in feces discharged by the wearer is absorbed by the core 4 which is present in the first through fourth sections 14, 15, 16, 17 after has permeated the topsheet 2. The core 4 which is present in the first and second sections 14, 15 contributes to improvement of a liquid-absorbing capacity in the concavity 19.

A liquid-absorbing function of the core 4 may be set to be higher in the third section 16 than in the first, second and fourth sections 14, 15, 17 to ensure that a large moisture content in loose passage can be rapidly absorbed by the core 4 in the third section 16 before loose passage flows to the front and rear waist regions 5, 7 as well as to the side flaps 10 and consequently it is possible to reliably prevent loose passage from flowing to the front and rear waist regions 5, 7 as well as to the side flaps 10.

Figure 7:
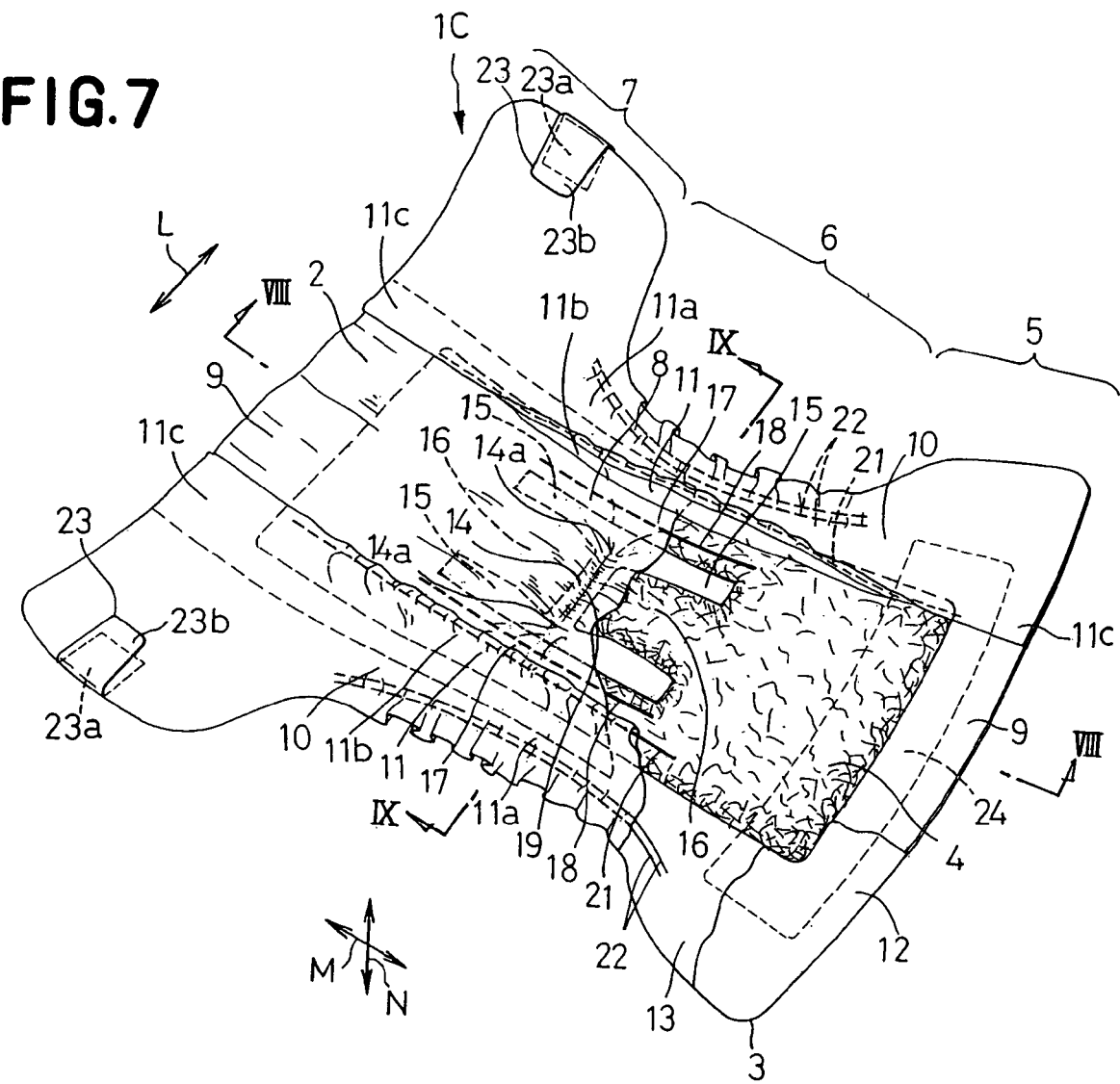
FIG. 7 is a partially cutaway perspective view showing still another embodiment of the diaper according to the invention.

FIG. 7 is a partially cutaway perspective view of a diaper 1C according to still another embodiment of the invention, FIG. 8 is a sectional view taken along the line VIII-VIII in FIG. 7 and FIG. 9 is a sectional view taken along the line IX-IX in FIG. 7. In FIG. 7, a transverse direction is indicated by an arrow L, a longitudinal direction is indicated by an arrow M and a thickness direction is indicated by an arrow N. FIG. 8 corresponds to the diaper 1C but not broken away.

The diaper 1C comprises a liquid-pervious topsheet 2, a liquid-impervious backsheet 3 and the semi-rigid liquid-absorbent core 4 interposed between these two sheets 2, 3. The backsheet 3 as well as the core 4 are same as those in FIG. 1. The diaper 1C is composed, as viewed in the longitudinal direction, of a front waist region 5, a rear waist region 7, a crotch region 6 extending between these two waist regions 5, 7. A liquid-absorbent zone 8 in which the core 4 functions to absorb body fluids discharged from a wearer, a pair of end flaps 9l extending in the transverse direction and a pair of side flaps 10 extending in the longitudinal direction. The liquid-absorbent zone 8 is formed in the front and rear waist regions 5, 7 and the crotch region 6 and has a stiffness higher than those of the end flaps 9 and the side flaps 10. The side flaps 10 are provided with a pair of liquid-impervious leak-barrier sheets 11.

The liquid-absorbent zone 8 in the front and rear waist regions 5, 7 is formed from the top- and backsheets 2, 3 and the core 4. In the front and rear waist regions 5, 7, the core 4 is permanently bonded to the inner surfaces of the top- and backsheets 2, 3. The liquid-absorbent zone 8 in the crotch region 6 has a first section 14 extending across the crotch region 6 at its longitudinal middle, a pair of second sections 15 lying transversely outside transversely opposite sides 14a of the first section 14 and longitudinally extending toward the front and rear waist regions 5, 7, a pair of third sections 16 lying between the respective second sections 15 and longitudinally extending from the first section 14 toward the front and rear waist regions 5, 7 and a pair of fourth sections 17 lying transversely outside the respective second sections 15 and extending in the longitudinal direction.

The first and second sections 14, 15 are formed from the top- and backsheets 2, 3 and do not contain the core 4. In the first and second sections 14, 15, the top- and backsheets 2, 3 have their inner surfaces permanently bonded to each other.

The third and fourth sections 16, 17 are formed from the top- and backsheets 2, 3 and the core 4. The third sections 16 are spaced from each other with the first section 14 therebetween and lie in generally front and rear halves, respectively, of the crotch region 6. The core 4 in the third sections 16 is contiguous to the core 4 in the front and rear waist regions 5, 7. In the third sections 16, the core 4 is bonded neither to the topsheet 2 nor to the backsheet 3, i.e., left free therefrom. In the third sections 16, it is alternatively possible to bond the core 4 to the inner surfaces of the top- and backsheets 2, 3 or any one of these top- and backsheets 2, 3.

The fourth sections 17 respectively lie between the side flaps 10 and the second sections 15. The core 4 in the fourth sections 17 is contiguous to the core 4 in the front and rear waist regions 5, 7. In the fourth sections 17, the core 4 is permanently bonded to the inner surfaces of the top- and backsheets 2, 3. Stretchably elastic members 18 extending in the longitudinal direction are contractibly attached to the respective fourth sections 17. These elastic members 18 are interposed between the topsheet 2 and the core 4 and permanently bonded to the inner surface of the topsheet 2 and to the core 4.

The liquid-absorbing function achieved by the core 4 in the third sections 16 may be equal to that achieved by the core 4 in the fourth sections 17 or the liquid-absorbing function achieved by the core 4 in the third sections 16 may be higher than that achieved by the core 4 in the fourth sections 17. Gurley stiffness values of the first through fourth sections 14, 15, 16, 17 as well as the method of measuring Gurley stiffness values of these sections 14, 15, 16, 17 are similar to those as have been described in reference with FIG. 1.

The core 4 is absent in the first and second sections 14, 15, resulting in a stiffness of these sections 14, 15 lower than that of the third and fourth sections 16, 17 and these sections 14, 15 are more flexible than the third and fourth sections 16, 17, i.e., high flexibility. In the liquid-absorbent zone 8 lying in the crotch region 6, a contractile force of the elastic members 18 in the longitudinal direction causes the fourth sections 17 to contract in the longitudinal direction and causes the third section 16 to get near to the first section 14. In the liquid-absorbent zone 8 lying in the crotch region 6, the first and second sections 14, 15 are longitudinally flexed downward in the thickness direction of the diaper 1C to form a concavity 19, i.e., feces pocket. This concavity 19 is defined by the first section 14 and a part of the second sections 15 between the pair of fourth sections 17. As will be apparent from FIG. 8, a portion 20 of the third section 16 lying adjacent the first section 14 slopes downward as viewed in the thickness direction of the diaper 1C and constitute a part of the concavity 19.

Each of the leak-barrier sheets 11 has a proximal portion 11a extending in the longitudinal direction, a distal portion 11b normally biased to rise up above the topsheet 2 and longitudinally opposite fixed ends 11c lying on the end flaps 9, respectively, and collapsed inward as viewed in the transverse direction of the diaper 1C. A stretchably elastic member 21 extending in the longitudinal direction is permanently attached to the leak-barrier sheet 11 in the vicinity of an upper edge of the distal portion 11b so that the elastic member 21 can contract in the longitudinal direction.

The end flaps 9 are formed from longitudinally opposite end portions 2a of the topsheet 2 and longitudinally opposite end portions 3a of the backsheets 3. In the end flaps 9, these end portions 2a, 3a of the top- and backsheets 2, 3 are put flat and permanently bonded together. The longitudinally opposite fixed ends 11c of the respective leak-barrier sheets 11 are permanently bonded to the outer surface of the topsheet 2. The side flaps 10 are formed from transversely opposite lateral portions 2b of the topsheet 2 and the transversely opposite lateral portions 3b of the backsheet 3, and the proximal portions 11a of the respective leak-barrier sheets 11. In each of the side flaps 10, the respective portions 2b, 3b, 11a of these sheets 2, 3, 11 are put flat and permanently bonded one to another. A plurality of leg elastic members 22 extending in the longitudinal direction are contractibly attached to each of the side flaps 10.

In the rear waist region 7, the side flaps 10 are provided with flexible tape fasteners 23 each having a free end portion 23b coated with adhesives (not shown). The front waist region 5 is provided with a flexible target tape strip 24 which is relatively long in the transverse direction and attached thereto so that the distal portions 23b of the respective tape fasteners 23 may be detachably anchored thereon. The tape fasteners 23 and the target tape strip 24 are made of plastic film. The procedure for putting this diaper 1C on the wearer's body is same as for the diaper 1A of FIG. 1.

In the crotch region 5 of this diaper 1C, the liquid-absorbent zone 8 is formed with the concavity 19 directed downward in the thickness direction so that feces discharged by the wearer of this diaper 1C may be contained in this concavity 19. The core 4 lying in the third and fourth sections 16, 17 forms a peripheral wall surrounding the concavity 19 and such peripheral wall is effective to prevent loose passage contained in the concavity 19 from flowing to the front and rear waist regions 5, 7 and to the side flaps 10. Moisture contained in feces discharged by the wearer is absorbed by the core 4 which is present in the third sections 16 after has permeated the topsheet 2.

The core 4 lying in the third section 16 is not bonded to the top- and backsheets 2, 3 and therefore it is unlikely that the contractile force of the elastic members 18 might be restrained by the stiffness of the core 4 in this third section 16. In other words, the second sections 15 can smoothly contracted in the longitudinal direction and the liquid-absorbent zone 8 lying in the crotch region 6 can reliably form the concavity 19.

With this diaper 1C, the liquid-absorbing function of the core 4 lying in the third sections 16 may be set to be higher than that of the core 4 lying in the fourth sections 17 to ensure that a large quantity of moisture contained in loose passage can be rapidly absorbed by the core 4 lying in the third sections 16 before loose passage flows to the front and rear waist regions 5, 7 and to the side flaps 10. In this way, the core 4 lying in the third sections 16 can reliably prevent loose passage from flowing to the front and rear waist regions 5, 7 as well as to the side flaps 10.

Stock materials for the topsheet 2 may be selected from a hydrophilic fibrous nonwoven fabric, a hydrophobic fibrous nonwoven fabric having a plurality of apertures and a plastic film having a plurality of fine perforations. Stock materials for the backsheet 3 may be selected from a hydrophobic fibrous nonwoven fabric, a breathable liquid-impervious plastic film and a composite sheet comprising two or more hydrophobic fibrous nonwoven fabric layers laminated one upon another. The leak-barrier sheet 11 may be made of the same material of which the backsheet 3 is made. Nonwoven fabric may be selected from those made by spun lace-, needle punch-, melt blown-, thermal bond-, spun bond- and chemical bond-processes.

As stock materials for the backsheet 3 and the leak-barrier sheet 11, it is also possible to use a composite nonwoven fabric (SM nonwoven fabric or SMS nonwoven fabric) consisting of a melt blown fibrous nonwoven fabric having a high water-resistance and a spun bond fibrous nonwoven fabric having a high strength and a high flexibility laminated on at least one side of the melt blown fibrous nonwoven fabric.

The hydrophilic fibrous nonwoven fabric may be made of any one of synthetic fiber, semi-synthetic fiber and regenerated fibers each modified to become hydrophilic or conjugate fibers thereof. While not specified, the synthetic fibers may be selected from polyester-, polyacrylonitrile-, polyvinyl chloride-, polyethylene-, polypropylene- and polystyrene-based fibers. The suitably useful synthetic fibers further include core-sheath type conjugate fibers, side-by-side type conjugate fibers, macaroni fibers, microporous fibers and end-to-end type conjugate fibers. The hydrophobic fibrous nonwoven fabric may contain therein semi-synthetic fibers or regenerated fibers both treated to become water repellent.

Preferably, the core 4 is entirely wrapped with a liquid-pervious sheet such as a tissue paper or a hydrophilic fibrous nonwoven fabric in order to prevent the core 4 from getting out of its initial shape. The super-absorbent polymer constituting the core 4 may be selected from a starch-based polymer, a cellulose-based polymer and a synthetic polymer. Such super-absorbent polymers may be particulate or fibrous.

Permanently bonding of the top- and backsheets 2, 3 to each other, permanently bonding of the leak-barrier sheets 11 to the top- and backsheets 2, 3, permanently bonding of the core 4 to the top- and backsheets 2, 3 and permanently bonding the elastic members 18, 21, 22 to the top- and backsheets 2, 3 and to the leak-barrier sheets 11 may be carried out using adhesive or welding techniques such as heat-sealing or ultrasonic sealing techniques.

Adhesives may be appropriately selected from a group consisting of a hot melt adhesive, an acrylic adhesive and elastomeric adhesive. The adhesives may be applied on the top- and backsheets 2, 3 and the leak-barrier sheets 11 in a suitable pattern selected from a spiral pattern, a zigzag pattern, a dotted pattern and a striped pattern. Application of the adhesives on these sheets 2, 3, 11 in such patter generates adhesive-coated regions and adhesive-free regions and consequently these sheets 2, 3, 11 are permanently bonded one to another in an intermittent fashion.

In the diapers 1A, 1B, 1C illustrated in FIGS. 1, 4 and 7, respectively, the elastic members 18 may be interposed between the backsheet 3 and the core 4 and permanently bonded to the inner surface of the backsheet 3 and the core 4.

In the case of the diapers 1A, 1C illustrated in FIGS. 1 and 7, respectively, the core 4 may be absent in the first and second sections 14, 15. In this case, the stiffness of the core 4 lying in the first and second sections 14, 15 may be set to be lower than the stiffness in the core 4 lying in the third and fourth sections 16, 17, as the diaper 1B of FIG. 4 is the case. In the diaper 1B of FIG. 4 also, the first and second sections 14, 15 may be formed from the top- and backsheets 2, 3 except the core 4, similarly to the diapers 1A, 1C illustrated by FIGS. 1 and 7, respectively. In the diapers 1A, 1C of FIGS. 1 and 7, the elastic members 18 may be contractibly attached not only to the fourth section 17 but also to the first and second sections 14, 15. When the elastic members 18 are attached to the first and second sections 14, 15 also, the elastic members 18 may be interposed between the top- and backsheets 2, 3 and permanently bonded to the inner surfaces of these sheets 2, 3.

The present invention is applicable not only to the so-called open-type diapers 1A, 1B, 1C with the front and rear waist regions adapted to be connected together immediately before put on the wearer's body but also to the so-called pants-type diaper having the front and rear waist regions previously connected together so as to the form the waist-hole and the leg-holes.

With the disposable diaper according to the present invention, the contractile force of the stretchably elastic members in the longitudinal direction causes the fourth section to contract in the longitudinal direction whereupon the first and second sections are flexed downward to form the liquid-absorbent zone in the crotch region with the concavity (feces pocket) which is concave in the thickness direction of the diaper. In this way, the diaper is capable of contain feces discharged by the wearer in this feces pocket. In this diaper, even when the contractile force of the elastic members intend to close the opening of the feces pocket, the stiffness of the third and fourth sections effectively restrain the contractile force of the elastic members and prevent the pocket of the feces pocket from being closed. In this way, feces can be reliably contained in the feces pocket. The diaper according to the invention is advantageous in that the core is less bulky than in conventional diapers of which the core overlaps itself. As a result, it is unlikely that the wearer of this diaper might experience any feeling of discomfort.

With the diaper of which the core has a liquid-absorbing function higher in the third section than in the fourth sections, a large moisture content in loose passage can be rapidly absorbed by the third section before loose passage flows to the front and rear waist regions as well as to the side flaps and consequently it is possible to reliably prevent loose passage from flowing to the front and rear waist regions as well as to the side flaps.

What is claimed is:

1. A disposable diaper having a longitudinal direction and a transverse direction, comprising:
   a liquid-pervious topsheet facing a wearer's skin;
   a liquid-impervious backsheet facing away from the wearer's skin;
   a liquid-absorbent core interposed between said top- and backsheets;
   a front waist region;
   a rear waist region;
   a crotch region extending between said front and rear waist regions;
   a liquid-absorbent zone being formed in said front and rear waist regions and said crotch region;
   a pair of elasticized side flaps lying outside transversely opposite side edges of said liquid-absorbent zone;
   said liquid-absorbent zone in said crotch region exclusively having:
   a first section, having a length, a width and a depth, the length of which is greater than its width and which length extends across said crotch region at a longitudinal middle thereof in the transverse direction,
   a pair of second sections, each having a length, a width and a depth, the length of each said second sections extending from transversely opposite ends of the length of said first section toward at least one of said front and rear waist regions in the longitudinal direction,
   a third section, located in a U-shaped region defined by the length of said first section in the transverse direction of said disposable diaper and the lengths of said second sections in the longitudinal direction of said disposable diaper, and
   a pair of fourth sections extending on a transverse outside of each of said second sections in the longitudinal direction;
   wherein said first and second sections are formed from said top sheet and said back sheet except said core and said third and fourth sections are formed from said top sheet and said back sheet and said core, so that each stiffness of said first and second sections is lower than that of said third and fourth sections;
   wherein said distal portion of said third section slopes downward as viewed in a thickness direction of the diaper; and
   wherein at least said fourth sections are provided with stretchably elastic members which contractibly extend in the longitudinal direction.

2. The diaper according to claim 1, wherein a liquid-absorbent function of said core is higher in said third section than in said fourth section.

3. The diaper according to claim 1, wherein a Gurley stiffness of said first and second sections is in a range of $0.98 \times 10^{-7}$ to $19.6 \times 10^{-7}$ N and a Gurley stiffness of said third and fourth sections is in a range of $9.8 \times 10^{-7}$ to $19.6 \times 10^{-7}$ N.

4. A disposable diaper having a longitudinal direction and a transverse direction, comprising:
   a liquid-pervious top sheet facing a wearer's skin;
   a liquid-impervious back sheet facing away from the wearer's skin;
   a liquid-absorbent core interposed between said top- and back sheets;
   a front waist region;
   a rear waist region;
   a crotch region extending between said front and rear waist regions;
   a liquid-absorbent zone being formed in said front and rear waist regions and said crotch region;
   a pair of elasticized side flaps lying outside transversely opposite side edges of said liquid-absorbent zone;
   said liquid-absorbent zone in said crotch region exclusively having:
   a first section, having a length, a width and a depth, the length of which is greater than its width and which length extends across said crotch region at a longitudinal middle thereof in the transverse direction,
   a pair of second sections, each having a length, a width and a depth, the length of each said second sections extending from transversely opposite ends of the length of said first section toward at least one of said front and rear waist regions in the longitudinal direction, a third section, located in a U-shaped region defined by the length of said first section in the tranverse direction of said disposable diaper and the lengths of said second sections in the longitudinal direction of said disposable diaper; and a pair of fourth sections extending on a transverse outside of each of said second sections in the longitudinal direction;

wherein said first through fourth sections are formed from said top sheet and said back sheet and said core and a stiffness of the core is lower in said first and second sections than in said third and fourth sections, so that each stiffness of said first and second sections is lower than that of said third and fourth sections;

wherein said distal portion of said third section slopes downward as viewed in a thickness direction of the diaper; and wherein at least said fourth sections are provided with stretchably elastic members which contractibly extend in the longitudinal direction.

5. The diaper according to claim 4, wherein a liquid-absorbent function of said core is higher in said third section than in said fourth section.

6. The diaper according to claim 4, wherein a Gurley stiffness of said first and second sections is in a range of $0.98 \times 10^{-7}$ to $19.6 \times 10^{-7}$N and a Gurley stiffness of said third and fourth sections is in a range of $9.8 \times 10^{-7}$ to $19.6 \times 10^{-7}$N.

7. A disposable diaper having a longitudinal direction, a longitudinal axis, a transverse direction, and a transverse axis, comprising:

a liquid-pervious top sheet facing a wearer's skin;

a liquid-impervious back sheet facing away from the wearer's skin;

a liquid-absorbent core interposed between said top sheet and said back sheet;

a front waist region;

a rear waist region;

a crotch region extending between said front and rear waist regions;

a liquid-absorbent zone being formed in said front and rear waist regions and said crotch region;

a pair of elasticized side flaps lying outside transversely opposite side edges of said liquid-absorbent zone;

said liquid-absorbent zone in said crotch region exclusively having:

a first section, having a length, a width and a depth, the length of which is greater than its width and which length extends across said crotch region at a longitudinal middle thereof in the transverse direction, a pair of second sections, each having a length, a width and a depth, the length of each of said second sections extending from transversely opposite ends of the length of said first section toward at least one of said front and rear waist regions in the longitudinal direction, a third section, located in a U-shaped region defined by the length of said first section in the tranverse direction of said disposable diaper and the lengths of said second sections in the longitudinal direction of said disposable diaper, and a pair of fourth sections extending on a transverse outside of each of said second sections in the longitudinal direction;

wherein said first and second sections are formed from said top sheet and said back sheet except said core and said third and fourth sections are formed from said top sheet and said back sheet and said core, so that each stiffness of said first and second sections is lower than that of said third and fourth sections;

wherein said distal portion of said third section slopes downward as viewed in a thickness direction of the diaper; and wherein at least said fourth sections are provided with stretchably elastic members which contractibly extend in the longitudinal direction.

8. The diaper according to claim 7, wherein a liquid-absorbent function of said core is higher in said third section than in said fourth section.

9. The diaper according to claim 7, wherein a Gurley stiffness of said first and second sections is in a range of $0.98 \times 10^{-7}$ to $19.6 \times 10^{-7}$N and a Gurley stiffness of said third and fourth sections is in a range of $9.8 \times 10^{-7}$ to $19.6 \times 10^{-7}$N.

10. The diaper according to claim 7, further comprising:

a pair of liquid-barrier sheets in the longitudinal direction on said side flaps, each of said liquid-barrier sheets having proximal portions attached to one of said side flaps, elasticized distal portions biased to rise up above said top sheet and longitudinally opposite ends.

11. The diaper according to claim 1, further comprising:

a pair of liquid-barrier sheets in the longitudinal direction on said side flaps, each of said liquid-barrier sheets having proximal portions attached to one of said side flaps, elasticized distal portions biased to rise up above said top sheet and longitudinally opposite ends.

12. The diaper according to claim 4, further comprising:

a pair of liquid-barrier sheets in the longitudinal direction on said side flaps, each of said liquid-barrier sheets having proximal portions attached to one of said side flaps, elasticized distal portions biased to rise up above said top sheet and longitudinally opposite ends.

13. A disposable diaper having a longitudinal direction, a longitudinal axis, a transverse direction, and a transverse axis, comprising:

a liquid-pervious topsheet facing a wearer's skin;

a liquid-impervious backsheet facing away from the wearer's skin;

a liquid-absorbent core interposed between said top- and backsheets;

a front waist region;

a rear waist region;

a crotch region extending between said front and rear waist regions;

a liquid-absorbent zone being formed in said front and rear waist regions and said crotch region;

a pair of elasticized side flaps lying outside transversely opposite side edges of said liquid-absorbent zone;

said topsheet, said backsheet, and said core defining a single U-shaped channel, when viewed from a direction that is perpendicular to both said longitudinal direction and said transverse direction, in which the core is absent and the topsheet is bonded to said backsheet, said U-shaped channel defined by (i) a base channel centered over and oriented parallel to the tranverse axis of said disposable diaper and by (ii) two parallel longitudinal channels, each originating at an opposite end of said base channel and extending toward said front waist region or said rear waist region, each longitudinal channel situated parallel to and equidistant from said longitudinal axis.

* * * * *